(12) United States Patent
Kikuchi

(10) Patent No.: US 11,484,215 B2
(45) Date of Patent: Nov. 1, 2022

(54) BLOOD PRESSURE MEASURING APPARATUS

(71) Applicant: NIHON KOHDEN CORPORATION, Tokyo (JP)

(72) Inventor: Yoshiharu Kikuchi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 388 days.

(21) Appl. No.: 16/497,679

(22) PCT Filed: Mar. 20, 2018

(86) PCT No.: PCT/JP2018/011077
§ 371 (c)(1),
(2) Date: Sep. 25, 2019

(87) PCT Pub. No.: WO2018/180787
PCT Pub. Date: Oct. 4, 2018

(65) Prior Publication Data
US 2021/0121078 A1 Apr. 29, 2021

(30) Foreign Application Priority Data
Mar. 30, 2017 (JP) .............................. JP2017-067958

(51) Int. Cl.
*A61B 5/02* (2006.01)
*A61B 5/0225* (2006.01)
(Continued)

(52) U.S. Cl.
CPC .......... *A61B 5/0225* (2013.01); *A61B 5/0215* (2013.01); *A61B 5/14552* (2013.01); *A61B 5/025* (2013.01)

(58) Field of Classification Search
CPC ......... A61B 5/02; A61B 5/025; A61B 5/0225; A61B 5/0215; A61B 5/14552
See application file for complete search history.

(56) References Cited

U.S. PATENT DOCUMENTS

2011/0152650 A1 6/2011 Donehoo et al.
2011/0226035 A1 9/2011 Date
(Continued)

FOREIGN PATENT DOCUMENTS

CN 102100552 A 6/2011
CN 103340618 A 10/2013
(Continued)

OTHER PUBLICATIONS

Japanese Office action issued in Patent Application No. 2017-067958 dated Nov. 17, 2020.
(Continued)

*Primary Examiner* — Marjan Fardanesh
(74) *Attorney, Agent, or Firm* — Pearne & Gordon LLP

(57) ABSTRACT

A blood pressure measuring apparatus for measuring a blood pressure of a subject using a cuff attached to the subject is equipped with an inflating mechanism—configured to increase an inner pressure of the cuff, a processor and a memory—configured to store instructions that is readable by the processor. As the instructions are executed by the processor, the blood pressure measuring apparatus-acquires a pulse rate of the subject while causing the inflating mechanism to increase the inner pressure of the cuff at a prescribed inflation speed, and compares the pulse rate as acquired to a prescribed pulse rate. The blood pressure measuring apparatus causes the inflating mechanism to increase the inner pressure of the cuff at an inflation speed that is lower than the prescribed inflation speed if the pulse rate as acquired is less than the prescribed pulse rate.

15 Claims, 3 Drawing Sheets

(51) Int. Cl.
  *A61B 5/0215* (2006.01)
  *A61B 5/1455* (2006.01)
  *A61B 5/025* (2006.01)

(56) References Cited

U.S. PATENT DOCUMENTS

| | | |
|---|---|---|
| 2011/0231152 A1 | 9/2011 | Kawabe |
| 2011/0238326 A1 | 9/2011 | Takahashi |
| 2011/0251500 A1 | 10/2011 | Sawanoi |
| 2011/0251501 A1 | 10/2011 | Sawanoi |
| 2011/0257538 A1 | 10/2011 | Sawanoi |
| 2011/0257539 A1 | 10/2011 | Sawanoi et al. |
| 2011/0257540 A1 | 10/2011 | Sawanoi et al. |
| 2016/0220195 A1 | 8/2016 | Abu-Tarif et al. |
| 2020/0288984 A1 | 9/2020 | Ariyama et al. |

FOREIGN PATENT DOCUMENTS

| | | |
|---|---|---|
| CN | 105286838 A | 2/2016 |
| JP | S63-281622 A | 11/1988 |
| JP | H10-137204 A | 5/1998 |
| JP | 2001-204698 A | 7/2001 |
| JP | 2002-034938 A | 2/2002 |
| JP | 2002-078685 A | 3/2002 |
| JP | 2005-185681 A | 7/2005 |
| JP | 2006-247216 A | 9/2006 |
| JP | 2010-167275 A | 8/2010 |
| WO | 2016-055356 A1 | 4/2016 |
| WO | 2017-169924 A1 | 10/2017 |

OTHER PUBLICATIONS

Chinese Office Action dated Sep. 1, 2021 issued in Patent Application No. 201880023475.9.
Japanese Decision of Dismissal of Amendment dated Aug. 24, 2021 issued in Patent Application No. 2017-067968.
Japanese Decision of Refusal of Office Action dated Aug. 24, 2021 issued in Patent Application No. 2017-067968.
International Search Report Issued in Patent Application No. PCT/JP2018/011077 dated Jun. 14, 2018.
Written Opinion Issued in Patent Application No. PCT/JP2018/011077 dated Jun. 14, 2018.
Japanese Office Action dated March 2, 201 issued in Patent Application No. 2017-067958.
Japanese Decision of Dismissal of Amendment dated Aug. 24, 2021 issued in Patent Application No. 2017-067958.
Japanese Decision of Refusal of Office Action dated Aug. 24, 2021 issued in Patent Application No. 2017-067958.

BLOOD PRESSURE MEASURING APPARATUS

TECHNICAL FIELD

The present disclosure relates to a blood pressure measuring apparatus for measuring a blood pressure of a subject using a cuff attached to the subject.

BACKGROUND ART

Japanese Patent Publication No. 2002-078685A discloses what is called an inflation blood pressure measuring apparatus for determining a systolic blood pressure etc. of a subject while increasing the inner pressure of a cuff attached to the subject. Inflation blood pressure measuring apparatus is discriminated from what is called deflation blood pressure measuring apparatus. As for the deflation blood pressure measuring apparatus, the inner pressure of a cuff is first increased to a pressure that is more than an estimated systolic blood pressure of a subject, and a systolic blood pressure etc. of the subject is determined while decreasing the inner pressure of the cuff.

SUMMARY OF INVENTION

Technical Problem

An object of the present disclosure is to make it easier to complete a measurement in a short time while keeping high the measurement reliability of an inflation blood pressure measuring apparatus of the above kind.

Solution to Problem

According to one aspect of the disclosure, there is provided a blood pressure measuring apparatus for measuring a blood pressure of a subject using a cuff attached to the subject, comprising:
  an inflating mechanism configured to increase an inner pressure of the cuff;
  a processor; and
  a memory configured to store instructions that is readable by the processor,
  wherein the blood pressure measuring apparatus is configured to, as the instructions are executed by the processor:
  acquire a pulse rate of the subject while causing the inflating mechanism to increase the inner pressure of the cuff at a prescribed inflation speed;
  compare the pulse rate as acquired to a prescribed pulse rate; and
  causing the inflating mechanism to increase the inner pressure of the cuff at an inflation speed that is lower than the prescribed inflation speed if the pulse rate as acquired is less than the prescribed pulse rate.

In general, a noninvasive blood pressure measurement is performed using information that relates to beating of an artery of a subject that is detected while a cuff is being inflated. Thus, a more reliable measurement result can be obtained as the number of pulsations detected during cuff inflation increases. If a pulse rate of a subject is low, however, there may occur a case that desired measurement reliability cannot be obtained because the internal pressure of the cuff reaches an inflation limit value before acquisition of a sufficient amount of information.

With the above configuration, the number of pulsations detected during the inflation is made equivalent to a number to be obtained when a subject having the prescribed pulse rate is subjected to a measurement at the prescribed inflation speed. Accordingly, it is possible to avoid a fresh start of the measurement due to the fact that the inflation limit pressure is reached before acquisition of sufficient pulsation information. This makes it easier to complete a measurement in a short time while keeping high the measurement reliability of the inflation blood pressure measuring apparatus.

According to one aspect of the disclosure, there is provided a blood pressure measuring apparatus for measuring a blood pressure of a subject using a cuff attached to the subject, comprising:
  an inflating mechanism configured to increase an inner pressure of the cuff;
  a processor; and
  a memory configured to store instructions that is readable by the processor,
  wherein the blood pressure measuring apparatus is configured to, as the instructions are executed by the processor:
  acquire at least one of a past pulse rate and a past pulse pressure of the subject that was recorded in a past measurement;
  determine an inflation speed on the basis of the at least one of the past pulse rate and the past pulse pressure as acquired;
  causing the inflating mechanism to increase the inner pressure of the cuff at the inflation speed as determined.

With the above configuration, the number of pulsations detected during inflation is made equivalent to a number to be obtained when a subject having the prescribed pulse rate is subjected to a measurement at the prescribed inflation speed. That is, in this example, a proper inflation speed of the cuff is set according to a pulse rate-related tendency of a subject. Accordingly, it is possible to prevent a situation that the inflation limit pressure is reached before acquisition of sufficient pulsation information due to the fact that a too high inflation speed is uniformly employed for a subject who is known in advance to have a relatively low pulse rate. Furthermore, the processing for acquiring a pulse rate in real time may be omitted. As a result, it becomes easier to complete a measurement in a short time while keeping high the measurement reliability of the inflation blood pressure measuring apparatus.

DESCRIPTION OF EMBODIMENTS

Figure 1:
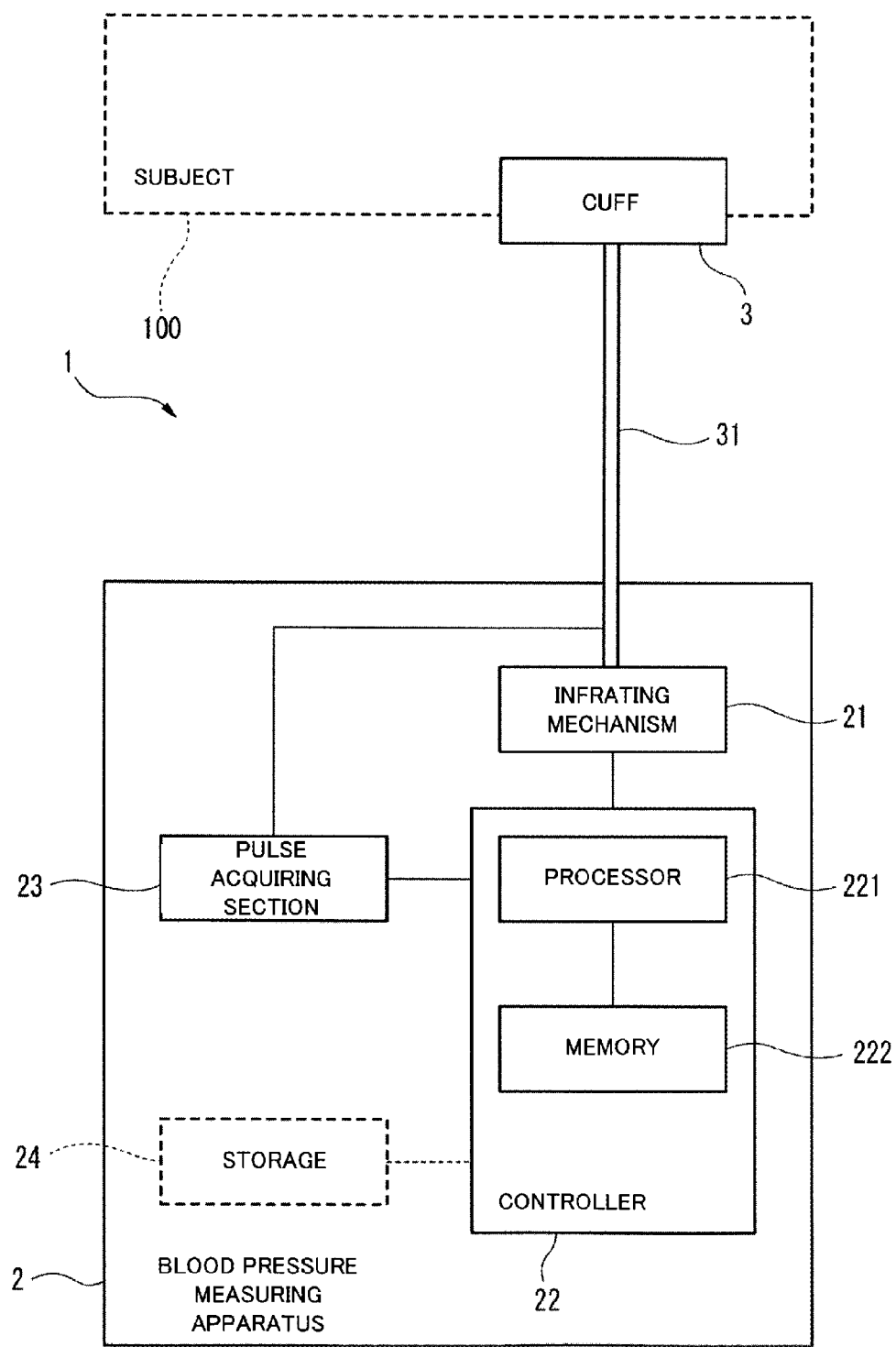
FIG. 1 illustrates a functional configuration of a blood pressure measuring system according to one embodiment.

Embodiments will be described below in detail with reference to the accompanying drawings. FIG. 1 shows the functional configuration of a blood pressure measuring system 1 according to the embodiment. The blood pressure measuring system 1 is comprises a blood pressure measuring apparatus 2 and a cuff 3.

The blood pressure measuring apparatus 2 is an apparatus for measuring a blood pressure of a subject 100 using the cuff 3 attached to the subject 100, and comprises an inflating mechanism 21, a controller 22, and a pulse acquiring section 23.

The inflating mechanism 21, which is connected to the cuff 3 by a tube 31, has a pump function and a valve function. The pump function serves to increase the internal pressure of the cuff 3 by sending air to it through the tube 31. The valve function serves to connect or disconnect the tube 31 to or from the external air. The internal pressure of the cuff 3 lowers if the tube 31 is connected to the external air in a state that the pump function is not in operation.

The controller 22 comprises processor 221 and a memory 222. As the processor 221, a CPU and an MPU can be exemplified. The processor 221 may include a plurality of cores. Examples of the memory 222 include a ROM and a RAM. The ROM may be stored with various computer-readable instructions. The processor 221 may designates at least a part of the instructions stored in the ROM that is to be executed on the RAM. The processor 221 may cooperate with the RAM in order to execute operations as described below in detail.

The pulse acquiring section 23 is implemented by a sensor that is connected to the cuff 3 attached to the body of the subject 100 and acquires a pulse rate of the subject 100. The pulse acquiring section 23 is configured to output a signal corresponding to a pulse rate of the subject 100. The signal that is output from the pulse acquiring section 23 is input to the controller 22.

Figure 2:
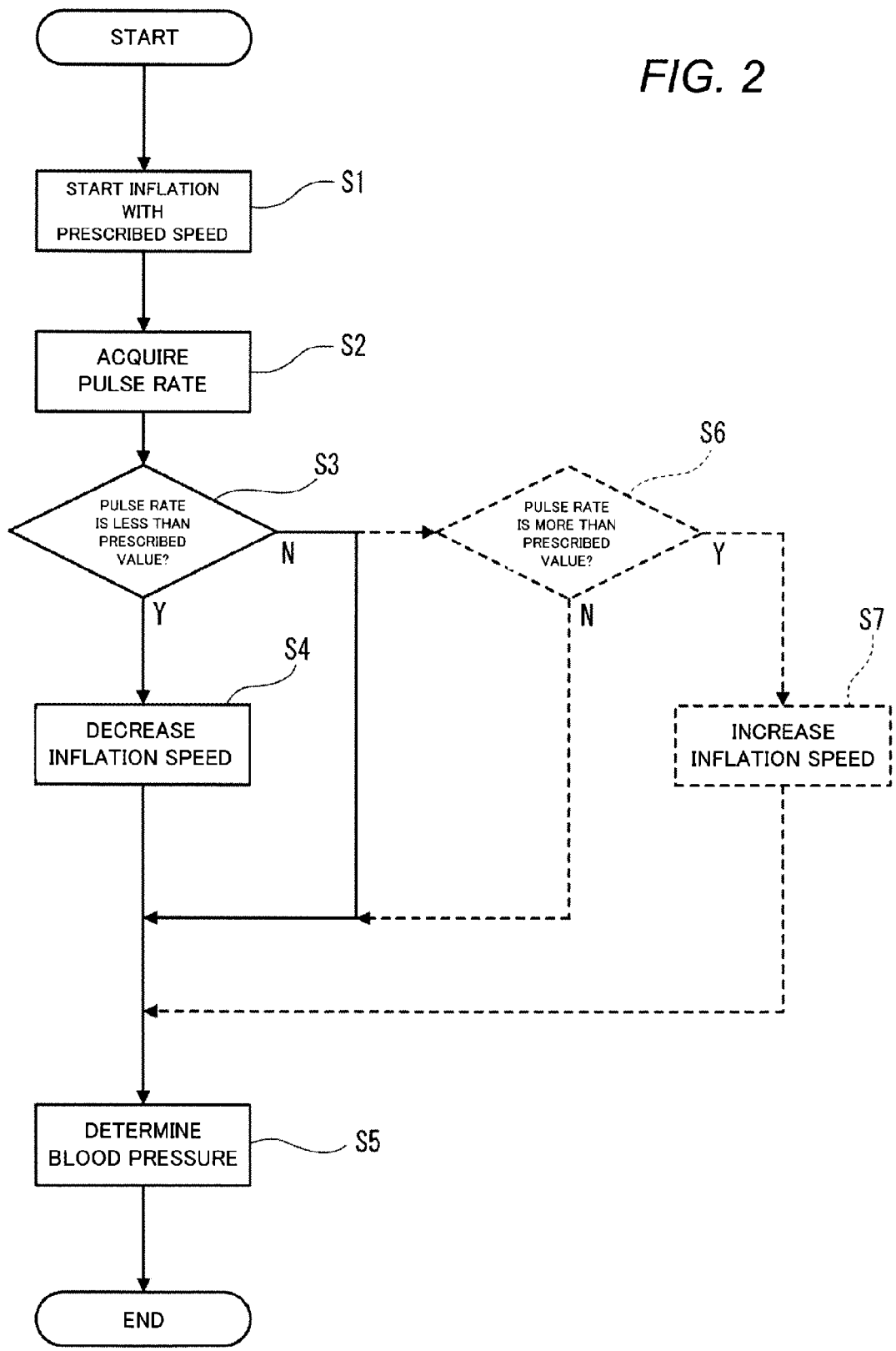
FIG. 2 illustrates an operation example of a blood pressure measuring apparatus shown in FIG. 1.

The blood pressure measuring apparatus 2 is configured to execute processing shown in FIG. 2 as instructions stored in the memory 222 are executed by the processor 221 in the controller 22.

First, at step S1, the blood pressure measuring apparatus 2 activates the pump function of the inflating mechanism 21 and thereby increases the internal pressure of the cuff 3 at a prescribed inflation speed (10 mmHg/sec, for example).

At step S2, the blood pressure measuring apparatus 2 acquires a pulse rate of the subject 100 via the pulse acquiring section 23. Alternatively, acquisition of a pulse rate may be started before the inflating operation of the inflating mechanism 21.

In general, a noninvasive blood pressure measurement is performed using information that relates to beating of an artery of a subject that is detected while a cuff is being inflated. Thus, a more reliable measurement result can be obtained as the number of pulsations detected during cuff inflation increases. If a pulse rate of a subject is low, however, there may occur a case that desired measurement reliability cannot be obtained because the internal pressure of the cuff reaches an inflation limit value before acquisition of a sufficient amount of information.

In view of the above, at step S3, the pulse rate acquired via the pulse acquiring section 23 is compared with a prescribed pulse rate (60 bpm, for example). The prescribed pulse rate is set at a value capable of providing desired measurement reliability.

If the pulse rate acquired via the pulse acquiring section 23 is lower than the prescribed pulse rate (S3: Y), at step S4 the blood pressure measuring apparatus 2 decreases the speed at which the inflating mechanism 21 inflates the cuff 3.

For example, if the acquired pulse rate is equal to 40 bpm, it is judged that desired measurement reliability cannot be obtained. The blood pressure measuring apparatus 2 determines a new inflation speed according to the following equation.

(new inflation speed)=(prescribed inflation speed)* (acquired pulse rate)/(prescribed pulse rate)

In the above-mentioned example, a new inflation speed is calculated as follows.

10 [mmHg/sec]*40 [bpm]/60 [bpm]=6.7 [mmHg/sec]

The blood pressure measuring apparatus 2 increases the internal pressure of the cuff 3 at the thus-determined inflation speed 6.7 mmHg/sec.

With the above configuration, the number of pulsations detected during the inflation is made equivalent to a number to be obtained when a subject having the prescribed pulse rate is subjected to a measurement at the prescribed inflation speed. Accordingly, it is possible to avoid a fresh start of the measurement due to the fact that the inflation limit pressure is reached before acquisition of sufficient pulsation information. This makes it easier to complete a measurement in a short time while keeping high the measurement reliability of the inflation blood pressure measuring apparatus 2.

At step S5, the blood pressure measuring apparatus 2 determines a blood pressure (at least one of a systolic blood pressure and a diastolic blood pressure) of the subject 100 by causing the inflating mechanism 21 to increase the internal pressure of the cuff 3 at the thus-changed inflation speed. Since the way of determining the blood pressure using the inflation blood pressure measuring apparatuses is known, it will not be described here in detail.

If the pulse rate acquired via the pulse acquiring section 23 is no less than the prescribed pulse rate (S3: N), at step S5 the blood pressure measuring apparatus 2 determines a blood pressure (at least one of a systolic blood pressure and a diastolic blood pressure) of the subject 100 by causing the inflating mechanism 21 to increase the internal pressure of the cuff 3 at the original inflation speed.

Alternatively, as indicated by dashed lines in FIG. 2, if the pulse rate acquired via the pulse acquiring section 23 is more than the prescribed pulse rate (S3: N; S6: Y), at step S7 the blood pressure measuring apparatus 2 may set the speed at which the inflating mechanism 21 inflates the cuff 3 lower than the original speed.

For example, if the acquired pulse rate is 80 bpm, the controller 22 determines a new inflation speed according to the above equation. That is, a new inflation speed is calculated as follows.

10 [mmHg/sec]*80 [bpm]/60 [bpm]=13.3 [mmHg/sec]

The blood pressure measuring apparatus 2 increases the internal pressure of the cuff 3 at the thus-determined inflation speed 13.3 mmHg/sec.

Although the inflating duration is shortened by the increase of the inflation speed, the number of pulsations detected during the inflation is equivalent to a number to be obtained when a subject having the prescribed pulse rate is subjected to a measurement at the prescribed inflation speed. This makes it easier to complete a measurement in a short time while keeping high the measurement reliability of the inflation blood pressure measuring apparatus 2.

As indicated by dashed lines in FIG. 1, the blood pressure measuring apparatus 2 may be equipped with a storage 24 that may be implemented by a semiconductor memory, a hard disk drive, or the like. The storage 24 may be configured to store past measurement data of the subject 100.

The past measurement data may include at least one of a pulse rate and a pulse pressure of the subject 100 that were recorded in a past blood pressure measurement. The pulse pressure is defined as the difference between a systolic blood pressure and a diastolic blood pressure. Alternatively, the past measurement data may include at least one of an average of pulse rates of the subject 100 that were recorded in a prescribed number of past blood pressure measurements and an average of pulse pressures of the subject 100 that were recorded in the prescribed number of past blood pressure measurements.

Figure 3:
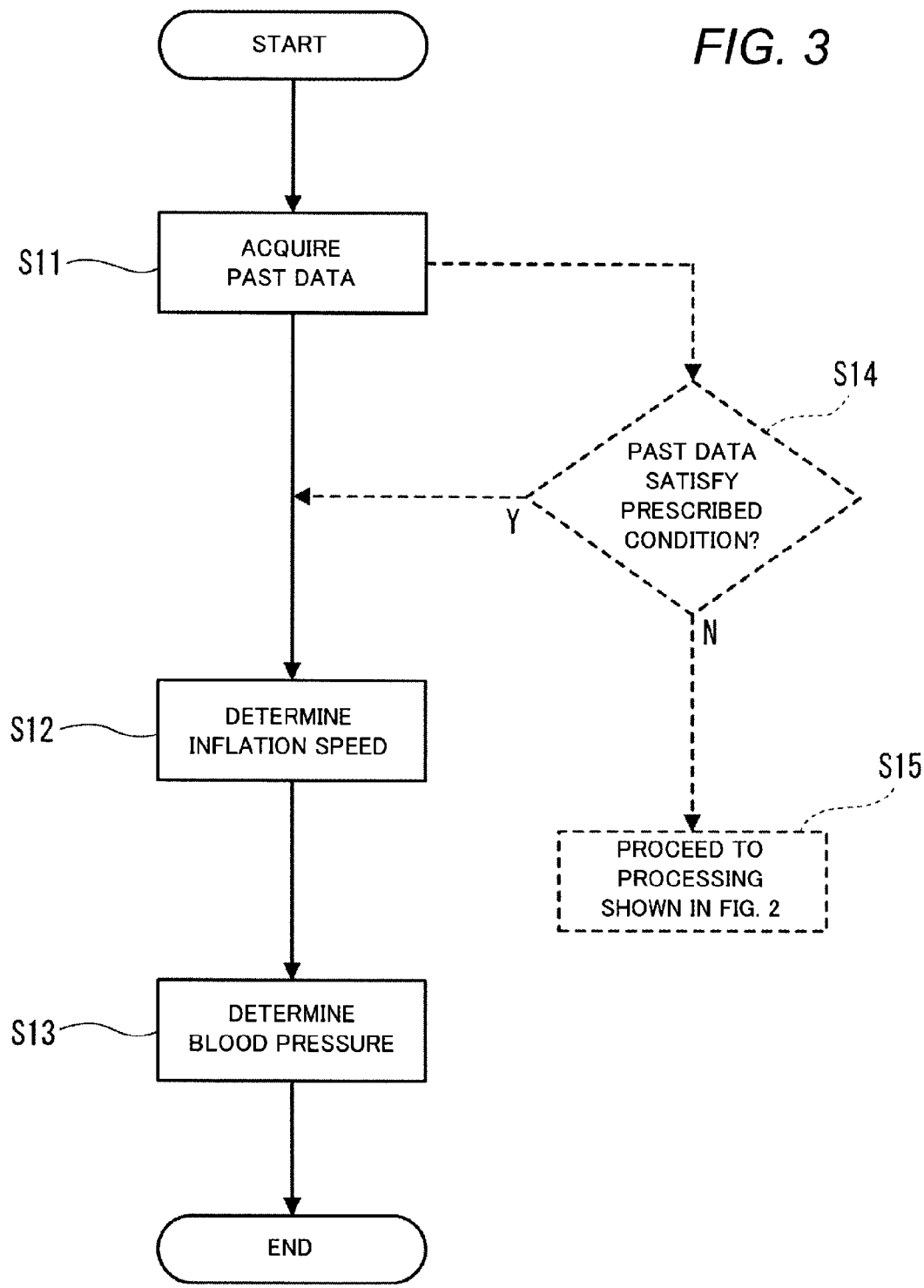
FIG. 3 illustrates an operation example of a blood pressure measuring apparatus shown in FIG. 1.

The thus-configured blood pressure measuring apparatus 2 may execute processing shown in FIG. 3 as instructions stored in the memory 222 are executed by the processor 221 in the controller 22.

First, at step S11, the blood pressure measuring apparatus 2 acquires past measurement data of the subject 100 stored in the storage 24.

At step S12, the blood pressure measuring apparatus 2 determines a speed at which the inflating mechanism 21 inflates the cuff 3 on the basis of the acquired past measurement data. Thus, the pulse acquiring section 23 is not necessary in determining an inflation speed.

Where the past measurement data include a pulse rate recorded in the past (or an average of pulse rates recorded in the past), the blood pressure measuring apparatus 2 determines an inflation speed according to the following equation.

(inflation speed)=(prescribed inflation speed)*(past pulse rate)/(prescribed pulse rate)

An example of the prescribed inflation speed is 10 mmHg/sec, and an example of the prescribed pulse rate is 60 bpm. The prescribed inflation speed and the prescribed pulse rate are set at values capable of providing desired measurement reliability.

For example, where the acquired past pulse rate is 40 bpm, an inflation speed is calculated as follows.

10 [mmHg/sec]*40 [bpm]/60 [bpm]=6.7 [mmHg]

The controller 22 increases the internal pressure of the cuff 3 at the thus-determined inflation speed 6.7 mmHg/sec.

With the above-described processing, the number of pulsations detected during inflation is made equivalent to a number to be obtained when a subject having the prescribed pulse rate is subjected to a measurement at the prescribed inflation speed. That is, in this example, a proper inflation speed of the cuff 3 is set according to a pulse rate-related tendency of a subject. Accordingly, it is possible to prevent a situation that the inflation limit pressure is reached before acquisition of sufficient pulsation information due to the fact that a too high inflation speed is uniformly employed for a subject who is known in advance to have a relatively low pulse rate. Furthermore, the step of acquiring a pulse rate in real time by the pulse acquiring section 23 is not necessary. As a result, it becomes easier to complete a measurement in a short time while keeping high the measurement reliability of the inflation blood pressure measuring apparatus 2.

Where the past measurement data include a pulse pressure recorded in the past (or an average of pulse pressures recorded in the past), the controller 22 determines an inflation speed according to the following equation.

(inflation speed)=(prescribed inflation speed)*(past pulse pressure)/(prescribed pulse pressure)

An example of the prescribed inflation speed is 10 mmHg/sec, and an example of the prescribed pulse pressure is 40 mmHg.

As mentioned above, in noninvasive blood pressure measurements, the pulse pressure is defined as the difference between a systolic blood pressure and a diastolic blood pressure. Thus, as the pulse pressure increases, the number of pulsations detected during inflation becomes larger and hence a measurement result is made more reliable. However, where the pulse pressure is low, desired measurement reliability may not be obtained because the internal pressure of the cuff 3 reaches the inflation limit pressure before acquisition of sufficient pulsation information. In view of this, the prescribed pulse pressure is set at a value capable of providing desired measurement reliability.

For example, where the acquired past pulse pressure is 30 mmHg, an inflation speed is calculated as follows.

10 [mmHg/sec]*30 [mmHg]/40 [mmHg]=7.5 [mmHg]

The controller 22 increases the internal pressure of the cuff 3 at the thus-determined inflation speed 7.5 mmHg/sec.

With the above-described processing, the number of pulsations detected during inflation is equivalent to a number to be obtained when a subject having the prescribed pulse pressure is subjected to a measurement at the prescribed inflation speed. That is, in this example, a proper inflation speed of the cuff 3 is set according to a tendency of a subject related to the pulse pressure. Thus, it is possible to prevent a situation that the inflation limit pressure is reached before acquisition of sufficient pulsation information due to the fact that a too high inflation speed is uniformly employed for a subject who is known in advance to have a relatively low pulse pressure. Furthermore, the step of acquiring a pulse rate in real time by the pulse acquiring section 23 is not necessary. As a result, it becomes easier to complete a measurement in a short time while keeping high the measurement reliability of the inflation blood pressure measuring apparatus 2.

Where the past measurement data include both of a pulse rate recorded in the past (or an average of pulse rates recorded in the past) and a pulse pressure recorded in the past (or an average of pulse pressures recorded in the past), the controller 22 determines an inflation speed according to the following equation.

(inflation speed)=(prescribed inflation speed)*[(past pulse rate)/(prescribed pulse rate)]*[(past pulse pressure)/(prescribed pulse pressure)]

For example, where the acquired past pulse rate is 40 bpm and the acquired past pulse pressure is 30 mmHg, an inflation speed is calculated as follows.

10 [mmHg/sec]*(40 [bpm]/60 [bpm])*(30 [mmHg]/ 40 [mmHg])=5 [mmHg]

The blood pressure measuring apparatus 2 increases the internal pressure of the cuff 3 at the thus-determined inflation speed 5 mmHg/sec.

At step S13, the blood pressure measuring apparatus 2 determines a blood pressure (at least one of a systolic blood pressure and a diastolic blood pressure) of the subject 100 by causing the inflating mechanism 21 to increase the internal pressure of the cuff 3 at the thus-determined inflation speed.

As indicated by dashed lines in FIG. 3, the blood pressure measuring apparatus 2 may judge at step S14 whether the past measurement data acquired from the storage 24 satisfy a prescribed condition (for example, a time period that has elapsed from a time point of recording of the past measurement data is no longer than a prescribed value). An example value of the prescribed time period is 30 minutes. However, the prescribed time period may be set as appropriate according to a condition of the subject 100 or a measurement environment. Other example values of the prescribed time period are one hour and one day.

If it is judged that the past measurement data acquired from the storage 24 satisfy the prescribed condition (S14: Y), the above-described step for determining the inflation speed is executed (S12).

On the other hand, if it is judged that the past measurement data acquired from the storage 24 do not satisfy the prescribed condition (S14: N), the processing proceeds to step S15, that is, the processing shown in FIG. 2. The blood pressure measuring apparatus 2 acquires a pulse rate via the pulse acquiring section 23 at step S2, compares the acquired pulse rate with the prescribed pulse rate at step S3, and determines an inflation speed at which the inflating mechanism 21 inflates the cuff 3 according to a comparison result.

In any of, for example, cases that a considerable time period has elapsed from a latest measurement, latest measurement data contain noise, subject's settings of the blood pressure measuring apparatus 2 have been altered, and the capacity of the cuff 3 has been changed, a current tendency of a subject (e.g., pulse rate or pulse pressure) may be different from one indicated by a result of the latest measurement. In such a case, it is not appropriate from the viewpoint of measurement reliability to employ an inflation speed that is determined on the basis of the past measurement.

With the above-described processing, as long as acquired past measurement data satisfy the prescribed condition and hence are reliable, the step of acquiring a pulse rate in real time by the pulse acquiring section 23 can be omitted to shorten the measurement duration. On the other hand, if acquired past measurement data do not satisfy the prescribed condition and hence are not reliable, a current (i.e., correct) pulse rate is acquired via the pulse acquiring section 23 and an inflation speed of the cuff 3 is determined on the basis of the thus-acquired pulse rate. The measurement reliability of the blood pressure measuring apparatus 2 can therefore be kept high.

The above-described embodiment is just an example for facilitating understanding of the present disclosure, and the configuration of the embodiment can be modified or improved as appropriate without departing from the fundamental concept of the present disclosure.

The inflating mechanism 21 and the controller 22 of the blood pressure measuring apparatus 2 need not always be disposed in a common casing. At least part of the functions of the controller 22 may be implemented by a computing device of a computer that is connected to the blood pressure measuring apparatus 2.

The controller 22 and the storage 24 of the blood pressure measuring apparatus 2 need not always be disposed in a common casing. Past measurement data stored in the storage 24 can be stored in a computer or a server on a network with which the controller 22 can communicate.

The pulse acquiring section 23 need not always be disposed in the blood pressure measuring apparatus 2, and may be configured to be attachable to the body of a subject.

For example, a pressure sensor may be provided in the cuff 3 so as to serve as the pulse acquiring section 23. In this case, no special devices other than the cuff 3 to be attached to a subject are necessary. Thus, not only can the configuration of the blood pressure measuring system 1 be simplified but also the time taken to prepare for a measurement can be shortened.

As a further alternative, at least one of a sensor used for measurement of a cardiogram, a sensor used for measurement of an arterial blood oxygen saturation, and an invasive blood pressure measuring apparatus may be used as the pulse acquiring section 23. In this case, the controller 22 acquires a pulse rate of the subject 100 on the basis of a signal corresponding to a pulse rate that is output from at least one of the above sensors and apparatus. Since pulse rate-related information to be used for acquiring another kind of physiological information is employed, pulse rate-related information that is relatively high in reliability can be acquired irrespective of the attachment state of the cuff 3. Where pieces of pulse rate-related information are acquired from plural sensor(s) and/or apparatus, the accuracy of pulse rate-related information can be increased further by, for example, comparing them.

The present application is based on Japanese Patent Application No. 2017-067958 filed on Mar. 30, 2017, the entire contents of which are hereby incorporated by reference.

What is claimed is:

1. An inflation blood pressure measuring apparatus for measuring a blood pressure of a subject using a cuff attached to the subject, comprising:
   an inflating mechanism configured to increase an inner pressure of the cuff;
   a processor; and
   a memory configured to store instructions that are readable by the processor, wherein the blood pressure measuring apparatus is configured to, as the instructions are executed by the processor:
   acquire a pulse rate of the subject while causing the inflating mechanism to increase the inner pressure of the cuff at a prescribed inflation speed;
   compare the pulse rate as acquired to a prescribed pulse rate;
   cause the inflating mechanism to increase the inner pressure of the cuff at an inflation speed that is lower than the prescribed inflation speed if the pulse rate as acquired is less than the prescribed pulse rate; and
   cause the inflating mechanism to increase the inner pressure of the cuff at an inflation speed that is higher than the prescribed inflation speed if the pulse rate as acquired is more than the prescribed pulse rate,
   wherein the inflation blood pressure measuring apparatus is configured to measure the blood pressure of the subject using the cuff while increasing the inner pressure of the cuff.

2. The inflation blood pressure measuring apparatus according to claim 1, wherein the pulse rate is acquired via at least one of: a sensor to be used for measurement of a cardiogram; a sensor to be used for measurement of an arterial blood oxygen saturation; and an invasive blood pressure measuring apparatus.

3. The inflation blood pressure measuring apparatus according to claim 1, wherein the pulse rate as acquired and the prescribed pulse rate are compared using an equation based on an inflation speed and a pulse rate.

4. The inflation blood pressure measuring apparatus according to claim 3, wherein the equation includes (the prescribed inflation speed)*(the pulse rate as acquired)/(the prescribed pulse rate).

5. The inflation blood pressure measuring apparatus according to claim 1, wherein the inflation speed is calculated by multiplying the prescribed inflation speed by the acquired pulse rate divided by the prescribed pulse rate.

6. An inflation blood pressure measuring apparatus for measuring a blood pressure of a subject using a cuff attached to the subject, comprising:
   an inflating mechanism configured to increase an inner pressure of the cuff;
   a processor; and a memory configured to store instructions that are readable by the processor, wherein the blood pressure measuring apparatus is configured to, as the instructions are executed by the processor:
acquire at least one of a past pulse rate and a past pulse pressure of the subject that was recorded in a past measurement;
determine an inflation speed on the basis of the at least one of the past pulse rate and the past pulse pressure as acquired; and
cause the inflating mechanism to increase the inner pressure of the cuff at the inflation speed as determined, wherein the inflation blood pressure measuring apparatus is configured to measure the blood pressure of the subject using the cuff while increasing the inner pressure of the cuff.

7. The inflation blood pressure measuring apparatus according to claim 6, wherein if the at least one of the past pulse rate and the past pulse pressure as acquired does not satisfy a prescribed condition, the blood pressure measuring apparatus is configured to:
acquire a pulse rate of the subject while causing the inflating mechanism to increase the inner pressure of the cuff at a prescribed inflation speed;
compare the pulse rate as acquired to a prescribed pulse rate; and
cause the inflating mechanism to increase the inner pressure of the cuff at an inflation speed that is lower than the prescribed inflation speed if the pulse rate as acquired is less than the prescribed pulse rate, or cause the inflating mechanism to increase the inner pressure of the cuff at an inflation speed that is higher than the prescribed inflation speed if the pulse rate as acquired is more than the prescribed pulse rate.

8. The inflation blood pressure measuring apparatus according to claim 7, wherein the prescribed condition comprises a time period that has elapsed from a time point of recording of the past measurement relative to a prescribed value.

9. The inflation blood pressure measuring apparatus according to claim 8, wherein acquiring a pulse rate in real-time is omitted so long as the past measurement satisfies the prescribed condition.

10. The inflation blood pressure measuring apparatus according to claim 7, wherein the prescribed condition comprises a time period including at least one of minutes, hours, or days.

11. The inflation blood pressure measuring apparatus according to claim 6, wherein the past pulse rate of the subject is acquired via at least one of: a sensor to be used for measurement of a cardiogram; a sensor to be used for measurement of an arterial blood oxygen saturation; and an invasive blood pressure measuring apparatus, and wherein the past pulse pressure of the subject is acquired via an invasive blood pressure measuring apparatus.

12. The inflation blood pressure measuring apparatus according to claim 6, wherein the pulse rate as acquired and the prescribed pulse rate are compared using an equation based on the at least one of the past pulse rate and the past pulse pressure of the subject that was recorded in the past measurement.

13. The inflation blood pressure measuring apparatus according to claim 12, wherein the equation includes (the prescribed inflation speed)*(the past pulse rate)/(the prescribed pulse rate) or (the prescribed inflation speed)*((the past pulse rate)/(the prescribed pulse rate))*((the past pulse pressure)/(the prescribed pulse pressure)).

14. The inflation blood pressure measuring apparatus according to claim 6, wherein the blood pressure measuring apparatus is configured to, as the instructions are executed by the processor: acquire, from a second memory, at least one of the past pulse rate and a past pulse pressure of the subject that was recorded in the past measurement to omit acquiring a pulse rate in real-time.

15. The inflation blood pressure measuring apparatus according to claim 6, wherein the blood pressure measuring apparatus is configured to, as the instructions are executed by the processor:
acquire the past pulse pressure of the subject that was recorded in the past measurement; and
determine an inflation speed on the basis of the past pulse pressure as acquired.

* * * * *